US009637634B2

(12) United States Patent
Jung et al.

(10) Patent No.: US 9,637,634 B2
(45) Date of Patent: May 2, 2017

(54) FLAME-RETARDANT POLYCARBONATE MOLDING MATERIALS V

(71) Applicant: Covestro Deutschland AG, Leverkusen (DE)

(72) Inventors: Mathieu Jung, Shanghai (CN); Thomas Eckel, Dormagen (DE); Vera Taschner, Langenfeld (DE)

(73) Assignee: Covestro Deutschland AG, Leverkusen (DE)

(*) Notice: Subject to any disclaimer, the term of this patent is extended or adjusted under 35 U.S.C. 154(b) by 0 days.

(21) Appl. No.: 14/649,686

(22) PCT Filed: Dec. 4, 2013

(86) PCT No.: PCT/EP2013/075487
§ 371 (c)(1),
(2) Date: Jun. 4, 2015

(87) PCT Pub. No.: WO2014/086830
PCT Pub. Date: Jun. 12, 2014

(65) Prior Publication Data
US 2016/0185956 A1 Jun. 30, 2016

(30) Foreign Application Priority Data
Dec. 7, 2012 (EP) .................................. 12196046

(51) Int. Cl.
C08L 69/00 (2006.01)
C07F 9/6581 (2006.01)
C08K 5/5399 (2006.01)

(52) U.S. Cl.
CPC .......... C08L 69/00 (2013.01); C07F 9/65814 (2013.01); C07F 9/65818 (2013.01); C08K 5/5399 (2013.01)

(58) Field of Classification Search
None
See application file for complete search history.

(56) References Cited

U.S. PATENT DOCUMENTS

| | | | |
|---|---|---|---|
| 6,433,082 B1 | 8/2002 | Eckel et al. | |
| 6,613,822 B1 | 9/2003 | Eckel et al. | |
| 6,740,695 B1 | 5/2004 | Eckel et al. | |
| 2003/0040643 A1 | 2/2003 | Nakano et al. | |
| 2003/0092802 A1 | 5/2003 | Nakacho et al. | |
| 2004/0039134 A1* | 2/2004 | Murakami | C08K 5/5399 525/410 |
| 2007/0060678 A1 | 3/2007 | Wenz et al. | |
| 2015/0299463 A1 | 10/2015 | Jung et al. | |
| 2015/0307705 A1 | 10/2015 | Jung et al. | |
| 2015/0307707 A1 | 10/2015 | Jung et al. | |
| 2015/0315381 A1 | 11/2015 | Jung et al. | |
| 2015/0329719 A1 | 11/2015 | Jung et al. | |

FOREIGN PATENT DOCUMENTS

| | | |
|---|---|---|
| DE | 19828535 | 12/1999 |
| DE | 19828536 | 12/1999 |
| DE | 19828539 | 12/1999 |
| DE | 19828541 | 12/1999 |
| DE | 10393198 B4 | 6/2010 |
| EP | 0728811 A2 | 8/1996 |
| EP | 1095097 A1 | 5/2001 |
| EP | 1095099 A1 | 5/2001 |
| EP | 1095100 A1 | 5/2001 |
| EP | 1196498 A1 | 4/2002 |
| JP | H04345657 | 12/1992 |
| JP | H0953009 A | 2/1997 |
| JP | 2000351893 A | 12/2000 |
| JP | 2001002908 A | 1/2001 |
| JP | 2004155802 A | 6/2004 |
| WO | 0000030 A1 | 1/2000 |
| WO | 0000541 A1 | 1/2000 |
| WO | 0000542 A1 | 1/2000 |
| WO | 0000544 A1 | 1/2000 |

OTHER PUBLICATIONS

International Search Report from corresponding PCT/EP2013/075487, mailed Apr. 7, 2014.
Database WPI Week 200131, Thomson Scientific, London, GB, XP002695686.
Database WPI, Thomson Scientific, London, GB, XP002695708.
International Search Report for International Application No. PCT/EP2013/075714, European Patent Office, Apr. 7, 2014.
International Search Report for International Application No. PCT/EP2013/075490, European Patent Office, Apr. 7, 2014.
International Search Report for International Application No. PCT/EP2013/075365, European Patent Office, Apr. 7, 2014.
International Search Report for International Application No. PCT/EP2013/075314, European Patent Office, Apr. 7, 2014.
International Search Report for International Application No. PCT/EP2013/075432, European Patent Office, Apr. 7, 2014.

* cited by examiner

Primary Examiner — Vu A Nguyen
(74) Attorney, Agent, or Firm — K&L Gates LLP

(57) ABSTRACT

The present invention relates to flame-retardant, impact-modified polycarbonate (PC) compositions and molding compositions which have good mechanical properties, good resistance to chemicals and high hydrolytic stability.

The present application additionally relates to the use of the compositions in the production of molded articles, and to molded articles produced from the compositions.

18 Claims, No Drawings

FLAME-RETARDANT POLYCARBONATE MOLDING MATERIALS V

CROSS REFERENCE TO RELATED APPLICATIONS

This application is a §371 National Stage Application of PCT/EP2013/075487, filed 4 Dec. 2013, which claims priority to EP 12196046.2, filed 7 Dec. 2012.

BACKGROUND

Field of the Invention

The present invention relates to flame-retardant, impact-modified polycarbonate (PC) compositions comprising cyclic phosphazenes, which compositions have high heat distortion resistance, very high notched impact strength, excellent flame resistance and high hydrolytic stability, and also to processes for their production, and to the use of cyclic phosphazenes as flame retardants in polycarbonate compositions.

Description of Related Art

EP0728811 A2 discloses polycarbonate/ABS moulding compositions comprising phosphazene as flame retardant. The moulding compositions have good flame retardancy, high impact strength, a high melt volume-flow rate and a high bending modulus.

JP 2000 351893 discloses impact-modified polycarbonate moulding compositions comprising phosphazenes, which compositions are distinguished by good hydrolytic stability, good flame retardancy and stability of the electrical properties.

EP 1 095 099 A1 describes polycarbonate/ABS moulding compositions provided with phosphazenes and phosphorus compounds, which compositions have excellent flame retardancy and very good mechanical properties such as joint line strength or notched impact strength.

EP 1 196 498 A1 describes moulding compositions provided with phosphazenes and based on polycarbonate and graft polymers selected from the group of the silicone, EP(D)M and acrylate rubbers as graft base, which compositions have excellent flame retardancy and very good mechanical properties such as stress cracking resistance or notched impact strength.

EP 1 095 100 A1 describes polycarbonate/ABS moulding compositions comprising phosphazenes and inorganic nanoparticles, which compositions have excellent flame retardancy and very good mechanical properties.

EP 1 095 097 A1 describes polycarbonate/ABS moulding compositions provided with phosphazenes, which compositions have excellent flame retardancy and very good processing properties, wherein the graft polymer is produced by means of mass, solution or mass-suspension polymerisation processes.

US2003/040643 A1 describes a process for the preparation of phenoxyphosphazenes, as well as polycarbonate/ABS moulding compositions comprising these phenoxyphosphazenes. The moulding compositions have good flame retardancy, good flowability, good impact strength and high heat distortion resistance.

In the above-mentioned documents, linear and cyclic phosphazenes are disclosed. In the case of the cyclic phosphazenes, the contents of trimers, tetramers and higher oligomers are not specified, however.

US 2003/092802 A1 discloses phenoxyphosphazenes, as well as their preparation and use in polycarbonate/ABS moulding compositions. The phenoxyphosphazenes are preferably crosslinked, and the moulding compositions are distinguished by good flame retardancy, good impact strength, a high bending modulus and a high melt volume-flow rate. The ABS used is not described more precisely. Moreover, the contents of trimers, tetramers and higher oligomers of the present application are not described in this document.

JP 2004 155802 discloses cyclic phosphazenes and their use in thermoplastic moulding compositions such as polycarbonate and ABS. Polycarbonate/ABS moulding compositions comprising cyclic phosphazenes with precisely defined contents of trimers, tetramers and higher oligomers are not disclosed.

JP 1995 0038462 describes polycarbonate compositions comprising graft polymers, phosphazenes as flame retardants and optionally vinyl copolymers. Specific structures, compositions and amounts of the flame retardant are not mentioned, however.

JP19990176718 describes thermoplastic compositions consisting of aromatic polycarbonate, copolymer of aromatic vinyl monomers and vinyl cyanides, graft polymer of alkyl (meth)acrylates and rubber, and phosphazene as flame retardant, which compositions have good flowability.

SUMMARY

Accordingly, the object of the present invention is to provide a flame-retardant moulding composition which is distinguished by a property combination of high heat distortion resistance, very high notched impact strength and high hydrolytic stability while having consistently good mechanical properties.

It is a further object of the invention to provide flame-retardant moulding compositions which, while having good flame retardancy, have only a low phosphazene content, because flame retardants represent a considerable cost factor in the production of these compositions, so that they become less expensive.

The moulding compositions are preferably flame retardant and fulfil the requirements of UL94 with V-0 even at thin wall thicknesses (i.e. wall thickness in the range from 1.0 mm to 1.5 mm).

It has been found, surprisingly, that the object of the present invention is achieved by compositions comprising
A) from 80 to 98 parts by weight, preferably from 85 to 97 parts by weight, more preferably from 88 to 96 parts by weight, of aromatic polycarbonate and/or aromatic polyester carbonate,
B) from 0.5 to 6.0 parts by weight, preferably from 1.0 to 5.0 parts by weight, particularly preferably from 1.5 to 4.0 parts by weight, of rubber-modified graft polymer,
C) from 0.8 to 5.0 parts by weight, preferably from 1.0 to 4.5 parts by weight, more preferably from 1.5 to 4.0 parts by weight, of at least one cyclic phosphazene of structure (X)

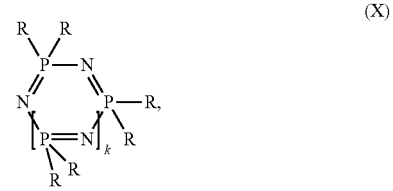

wherein
- k represents 1 or an integer from 1 to 10, preferably a number from 1 to 8, particularly preferably from 1 to 5, having a trimer content (k=1) of from 60 to 98 mol %, more preferably from 65 to 95 mol %, particularly preferably from 65 to 90 mol % and most particularly preferably from 65 to 85 mol %, in particular from 70 to 85 mol %, based on component C, and wherein
- R is in each case identical or different and represents an amine radical; $C_1$- to $C_8$-alkyl, preferably methyl, ethyl, propyl or butyl, each optionally halogenated, preferably halogenated with fluorine; $C_1$- to $C_8$-alkoxy, preferably methoxy, ethoxy, propoxy or butoxy; $C_5$- to $C_6$-cycloalkyl each optionally substituted by alkyl, preferably $C_1$-$C_4$-alkyl, and/or by halogen, preferably chlorine and/or bromine; $C_6$- to $C_{20}$-aryloxy, preferably phenoxy, naphthyloxy, each optionally substituted by alkyl, preferably $C_1$-$C_4$-alkyl, and/or by halogen, preferably chlorine, bromine, and/or by hydroxy; $C_7$- to $C_{12}$-aralkyl, preferably phenyl-$C_1$-$C_4$-alkyl, each optionally substituted by alkyl, preferably $C_1$-$C_4$-alkyl, and/or by halogen, preferably chlorine and/or bromine; or a halogen radical, preferably chlorine; or an OH radical, D) from 0 to 5.0 parts by weight, preferably from 0.5 to 4.0 parts by weight, more preferably from 1.0 to 3.0 parts by weight, of rubber-free vinyl (co)polymer or polyalkylene terephthalate, E) from 0 to 15.0 parts by weight, preferably from 0.05 to 12.00 parts by weight, more preferably from 0.2 to 10.0 parts by weight, particularly preferably from 0.4 to 5.0 parts by weight, of additives, F) from 0.05 to 1.00 part by weight, preferably from 0.1 to 0.8 part by weight, particularly preferably from 0.1 to 0.6 part by weight, of antidripping agents, wherein all parts by weight are preferably so normalised in the present application that the sum of the parts by weight of all the components A+B+C+D+E+F in the composition is 100.

DETAILED DESCRIPTION OF A PREFERRED EMBODIMENT

In a preferred embodiment, the composition consists only of components A to F.

In a preferred embodiment, the composition is free of inorganic flame retardants and flame-retardant synergists, in particular aluminium hydroxide, aluminium oxide hydroxide and arsenic and antimony oxides.

In a preferred embodiment, the composition is free of further organic flame retardants, in particular bisphenol A diphosphate oligomers, resorcinol diphosphate oligomers, triphenyl phosphate, octamethyl-resorcinol diphosphate and tetrabromo-bisphenol A diphosphate oligocarbonate.

The preferred embodiments can be carried out individually or in combination with one another.

The invention likewise provides processes for the production of the moulding compositions, and the use of the moulding compositions in the production of moulded articles, and the use of cyclic phosphazenes with a defined oligomer distribution in the production of the compositions according to the invention.

The moulding compositions according to the invention can be used in the production of moulded articles of any kind. These can be produced by injection moulding, extrusion and blow moulding processes. A further form of processing is the production of moulded articles by deep drawing from previously produced sheets or films.

Examples of such moulded articles are films, profiles, casing parts of any kind, for example for domestic appliances such as juice extractors, coffee machines, mixers; for office machines such as monitors, flat screens, notebooks, printers, copiers; sheets, tubes, conduits for electrical installations, windows, doors and further profiles for the construction sector (interior fitting and external applications) as well as parts for electronics and electrical engineering, such as switches, plugs and sockets, as well as bodywork and interior components for commercial vehicles, in particular for the automotive sector.

In particular, the moulding compositions according to the invention can also be used, for example, in the production of the following moulded articles or mouldings: Parts for the interior finishing of railway vehicles, ships, aircraft, buses and other motor vehicles, casings for electrical devices containing small transformers, casings for devices for processing and transmitting information, casings and coverings for medical devices, casings for security devices, mouldings for sanitary and bathroom fittings, cover grids for ventilator openings, and casings for garden equipment.

Component A

Aromatic polycarbonates and/or aromatic polyester carbonates according to component A that are suitable according to the invention are known in the literature or can be prepared by processes known in the literature (for the preparation of aromatic polycarbonates see, for example, Schnell, "Chemistry and Physics of Polycarbonates", Interscience Publishers, 1964 and DE-AS 1 495 626, DE-A 2 232 877, DE-A 2 703 376, DE-A 2 714 544, DE-A 3 000 610, DE-A 3 832 396; for the preparation of aromatic polyester carbonates see e.g. DE-A 3 007 934).

The preparation of aromatic polycarbonates is carried out, for example, by reaction of diphenols with carbonic acid halides, preferably phosgene, and/or with aromatic dicarboxylic acid dihalides, preferably benzenedicarboxylic acid dihalides, according to the interfacial process, optionally using chain terminators, for example monophenols, and optionally using branching agents having a functionality of three or more than three, for example triphenols or tetraphenols. Preparation by a melt polymerisation process by reaction of diphenols with, for example, diphenyl carbonate is also possible.

Diphenols for the preparation of the aromatic polycarbonates and/or aromatic polyester carbonates are preferably those of formula (I)

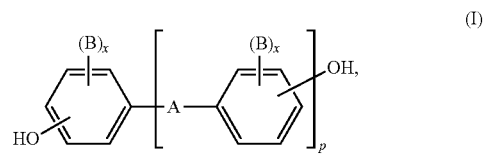

(I)

wherein

A is a single bond, $C_1$- to $C_5$-alkylene, $C_2$- to $C_5$-alkylidene, $C_5$- to $C_6$-cyclo-alkylidene, —O—, —SO—, —CO—, —S—, —SO$_2$—, $C_6$- to $C_{12}$-arylene, to which further aromatic rings optionally containing heteroatoms can be fused, or a radical of formula (II) or (III)

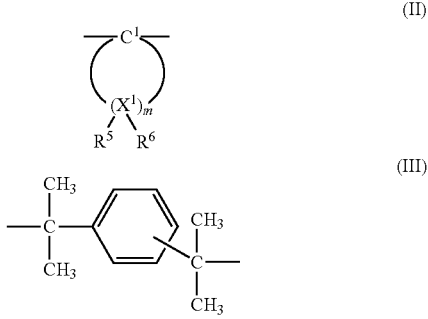

B is in each case $C_1$- to $C_{12}$-alkyl, preferably methyl, halogen, preferably chlorine and/or bromine, x each independently of the other is 0, 1 or 2, p is 1 or 0, and $R^5$ and $R^6$ can be chosen individually for each $X^1$ and each independently of the other is hydrogen or $C_1$- to $C_6$-alkyl, preferably hydrogen, methyl or ethyl, $X^1$ is carbon and m is an integer from 4 to 7, preferably 4 or 5, with the proviso that on at least one atom $X^1$, $R^5$ and $R^6$ are simultaneously alkyl.

Preferred diphenols are hydroquinone, resorcinol, dihydroxydiphenols, bis-(hydroxyphenyl)-$C_1$-$C_5$-alkanes, bis-(hydroxyphenyl)-$C_5$-$C_6$-cycloalkanes, bis-(hydroxyphenyl) ethers, bis-(hydroxyphenyl) sulfoxides, bis-(hydroxyphenyl) ketones, bis-(hydroxyphenyl)-sulfones and α,α-bis-(hydroxy-phenyl)-diisopropyl-benzenes, and derivatives thereof brominated and/or chlorinated on the ring.

Particularly preferred diphenols are 4,4'-dihydroxydiphenyl, bisphenol A, 2,4-bis(4-hydroxy-phenyl)-2-methylbutane, 1,1-bis-(4-hydroxyphenyl)-cyclohexane, 1,1-bis-(4-hydroxyphenyl)-3,3,5-trimethylcyclohexane, 4,4'-dihydroxydiphenyl sulfide, 4,4'-dihydroxydiphenylsulfone and di- and tetra-brominated or chlorinated derivatives thereof, such as, for example, 2,2-bis(3-chloro-4-hydroxyphenyl)-propane, 2,2-bis-(3,5-dichloro-4-hydroxyphenyl)-propane or 2,2-bis-(3,5-dibromo-4-hydroxyphenyl)-propane. 2,2-Bis-(4-hydroxyphenyl)-propane (bisphenol A) is particularly preferred.

The diphenols can be used on their own or in the form of arbitrary mixtures. The diphenols are known in the literature or are obtainable according to processes known in the literature.

Chain terminators suitable for the preparation of thermoplastic aromatic polycarbonates are, for example, phenol, p-chlorophenol, p-tert-butylphenol or 2,4,6-tribromophenol, but also long-chained alkylphenols, such as 4-[2-(2,4,4-trimethylpentyl)]-phenol, 4-(1,3-tetramethylbutyl)-phenol according to DE-A 2 842 005 or monoalkylphenol or dialkylphenols having a total of from 8 to 20 carbon atoms in the alkyl substituents, such as 3,5-di-tert-butylphenol, p-isooctylphenol, p-tert-octylphenol, p-dodecylphenol and 2-(3,5-dimethylheptyl)-phenol and 4-(3,5-dimethylheptyl)-phenol. The amount of chain terminators to be used is generally from 0.5 mol % to 10 mol %, based on the molar sum of the diphenols used in a particular case.

The thermoplastic aromatic polycarbonates have mean molecular weights (weight-average $M_w$, measured by GPC (gel permeation chromatography) with polycarbonate standard) of from 15,000 to 80,000 g/mol, preferably from 19,000 to 32,000 g/mol, particularly preferably from 22,000 to 30,000 g/mol.

The thermoplastic aromatic polycarbonates can be branched in a known manner, preferably by the incorporation of from 0.05 to 2.0 mol %, based on the sum of the diphenols used, of compounds having a functionality of three or more than three, for example those having three or more phenolic groups. Preference is given to the use of linear polycarbonates, more preferably based on bisphenol A.

Both homopolycarbonates and copolycarbonates are suitable. For the preparation of copolycarbonates of component A according to the invention it is also possible to use from 1 to 25 wt. %, preferably from 2.5 to 25 wt. %, based on the total amount of diphenols to be used, of polydiorganosiloxanes having hydroxyaryloxy end groups. These are known (U.S. Pat. No. 3,419,634) and can be prepared according to processes known in the literature. Also suitable are copolycarbonates containing polydiorganosiloxanes; the preparation of copolycarbonates containing polydiorganosiloxanes is described, for example, in DE-A 3 334 782.

Aromatic dicarboxylic acid dihalides for the preparation of aromatic polyester carbonates are preferably the diacid dichlorides of isophthalic acid, terephthalic acid, diphenyl ether 4,4'-dicarboxylic acid and naphthalene-2,6-dicarboxylic acid.

Mixtures of the diacid dichlorides of isophthalic acid and terephthalic acid in a ratio of from 1:20 to 20:1 are particularly preferred.

In the preparation of polyester carbonates, a carbonic acid halide, preferably phosgene, is additionally used concomitantly as bifunctional acid derivative.

Suitable chain terminators for the preparation of the aromatic polyester carbonates, in addition to the monophenols already mentioned, are also the chlorocarbonic acid esters thereof and the acid chlorides of aromatic monocarboxylic acids, which can optionally be substituted by $C_1$- to $C_{22}$-alkyl groups or by halogen atoms, as well as aliphatic $C_2$- to $C_{22}$-monocarboxylic acid chlorides.

The amount of chain terminators is in each case from 0.1 to 10 mol %, based in the case of phenolic chain terminators on mol of diphenol and in the case of monocarboxylic acid chloride chain terminators on mol of dicarboxylic acid dichloride.

One or more aromatic hydroxycarboxylic acids can additionally be used in the preparation of aromatic polyester carbonates.

The aromatic polyester carbonates can be both linear and branched in known manner (see in this connection DE-A 2 940 024 and DE-A 3 007 934), linear polyester carbonates being preferred.

There can be used as branching agents, for example, carboxylic acid chlorides having a functionality of three or more, such as trimesic acid trichloride, cyanuric acid trichloride, 3,3'-,4,4'-benzophenone-tetracarboxylic acid tetrachloride, 1,4,5,8-naphthalenetetracarboxylic acid tetrachloride or pyromellitic acid tetrachloride, in amounts of from 0.01 to 1.0 mol % (based on dicarboxylic acid dichlorides used), or phenols having a functionality of three or more, such as phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis[4,4-bis(4-hydroxy-phenyl)-cyclohexyl]-propane, 2,4-bis(4-hydroxyphenyl-isopropyl)-phenol, tetra-(4-hydroxyphenyl)-methane, 2,6-bis(2-hydroxy-5-methyl-benzyl)-4-methyl-phenol, 2-(4-hydroxyphenyl)-2-(2,4-dihydroxyphenyl)-propane, tetra-(4-[4-hydroxyphenyl-isopropyl]-phenoxy)-methane, 1,4-bis[4, 4'-dihydroxytriphenyl)-methyl]-benzene, in amounts of from 0.01 to 1.0 mol %, based on diphenols used. Phenolic branching agents can be placed in a vessel with the diphenols; acid chloride branching agents can be introduced together with the acid dichlorides.

The content of carbonate structural units in the thermoplastic aromatic polyester carbonates can vary as desired. The content of carbonate groups is preferably up to 100 mol %, in particular up to 80 mol %, particularly preferably up to 50 mol %, based on the sum of ester groups and carbonate groups. Both the esters and the carbonates contained in the aromatic polyester carbonates can be present in the polycondensation product in the form of blocks or distributed randomly.

The thermoplastic aromatic polycarbonates and polyester carbonates can be used on their own or in an arbitrary mixture.

Component B

The graft polymers B comprise, for example, graft polymers with rubber-elastic properties, which are obtainable substantially from at least 2 of the following monomers: chloroprene, 1,3-butadiene, isoprene, styrene, acrylonitrile, ethylene, propylene, vinyl acetate and (meth)acrylic acid esters having from 1 to 18 carbon atoms in the alcohol component; that is to say, polymers as are described, for example, in "Methoden der Organischen Chemie" (Houben-Weyl), Vol. 14/1, Georg Thieme-Verlag, Stuttgart 1961, p. 393-406 and in C. B. Bucknall, "Toughened Plastics", Appl. Science Publishers, London 1977.

Particularly preferred polymers B are, for example, ABS polymers (emulsion, mass and suspension ABS), as are described, for example, in DE-OS 2 035 390 (U.S. Pat. No. 3,644,574) or in DE-OS 2 248 242 (=GB-PS 1 409 275) or in Ullmanns, Enzyklopädie der Technischen Chemie, Vol. 19 (1980), p. 280 ff.

The graft copolymers B are produced by radical polymerisation, for example by emulsion, suspension, solution or mass polymerisation, preferably by emulsion or mass polymerisation.

Preferred polymers B are partially crosslinked and have gel contents (measured in toluene) of over 20 wt. %, preferably over 40 wt. %, in particular over 60 wt. %.

The gel content is determined at 25° C. in a suitable solvent (M. Hoffmann, H. Krömer, R. Kuhn, Polymeranalytik I and II, Georg Thieme-Verlag, Stuttgart 1977).

Preferred graft polymers B include graft polymers of:
B.1) from 5 to 95 parts by weight, preferably from 30 to 80 parts by weight, of a mixture of
B.1.1) from 50 to 95 parts by weight of styrene, α-methylstyrene, styrene substituted on the ring by methyl, $C_1$-$C_8$-alkyl methacrylate, in particular methyl methacrylate, $C_1$-$C_8$-alkyl acrylate, in particular methyl acrylate, or mixtures of these compounds, and
B.1.2) from 5 to 50 parts by weight of acrylonitrile, methacrylonitrile, $C_1$-$C_8$-alkyl methacrylates, in particular methyl methacrylate, $C_1$-$C_8$-alkyl acrylate, in particular methyl acrylate, maleic anhydride, $C_1$-$C_4$-alkyl- or -phenyl-N-substituted maleimides or mixtures of these compounds on
B.2) from 5 to 95 parts by weight, preferably from 20 to 70 parts by weight, of a rubber-containing graft base.

The graft base preferably has a glass transition temperature below −10° C.

Unless indicated otherwise in the present invention, glass transition temperatures are determined by means of differential scanning calorimetry (DSC) according to standard DIN EN 61006 at a heating rate of 10 K/min with definition of the Tg as the mid-point temperature (tangent method) and nitrogen as protecting gas.

Particular preference is given to a graft base based on a polybutadiene rubber.

Preferred graft polymers B are, for example, polybutadienes, butadiene/styrene copolymers and acrylate rubbers grafted with styrene and/or acrylonitrile and/or (meth)acrylic acid alkyl esters; that is to say, copolymers of the type described in DE-OS 1 694 173 (U.S. Pat. No. 3,564,077); polybutadienes, butadiene/styrene or butadiene/acrylonitrile copolymers, polyisobutenes or polyisoprenes grafted with acrylic or methacrylic acid alkyl esters, vinyl acetate, acrylonitrile, styrene and/or alkylstyrenes, as are described, for example, in DE-OS 2 348 377 (U.S. Pat. No. 3,919,353).

Particularly preferred graft polymers B are graft polymers obtainable by graft reaction of
I. from 10 to 70 wt. %, preferably from 15 to 50 wt. %, in particular from 20 to 40 wt. %, based on graft product, of at least one (meth)acrylic acid ester or from 10 to 70 wt. %, preferably from 15 to 50 wt. %, in particular from 20 to 40 wt. %, of a mixture of from 10 to 50 wt. %, preferably from 20 to 35 wt. %, based on the mixture, of acrylonitrile or (meth)acrylic acid ester and from 50 to 90 wt. %, preferably from 65 to 80 wt. %, based on the mixture, of styrene on
II. from 30 to 90 wt. %, preferably from 40 to 85 wt. %, in particular from 50 to 80 wt. %, based on graft product, of a butadiene polymer having at least 50 wt. %, based on II, butadiene radicals as graft base.

According to the invention, most particular preference is given to the use of ABS (acrylonitrile-butadiene-styrene) as the graft polymer.

The gel content of this graft base II is preferably at least 70 wt. % (measured in toluene), the degree of grafting G is from 0.15 to 0.55 and the mean particle diameter $d_{50}$ of the graft polymer B is from 0.05 to 2 μm, preferably from 0.1 to 0.6 μm.

(Meth)acrylic acid esters I are esters of acrylic acid or methacrylic acid and monohydric alcohols having from 1 to 18 carbon atoms. Methacrylic acid methyl esters, ethyl esters and propyl esters are particularly preferred.

As well as comprising butadiene radicals, the graft base II can comprise up to 50 wt. %, based on II, of radicals of other ethylenically unsaturated monomers, such as styrene, acrylonitrile, esters of acrylic or methacrylic acid having from 1 to 4 carbon atoms in the alcohol component (such as methyl acrylate, ethyl acrylate, methyl methacrylate, ethyl methacrylate), vinyl esters and/or vinyl ethers. The preferred graft base II consists of pure polybutadiene.

Because, as is known, the graft monomers are not necessarily grafted completely onto the graft base during the graft reaction, graft polymers B are also understood according to the invention as being those products that are obtained by polymerisation of the graft monomers in the presence of the graft base.

The degree of grafting G denotes the weight ratio of grafted graft monomers to the graft base and is dimensionless.

The mean particle size $d_{50}$ is the diameter above and below which in each case 50 wt. % of the particles lie. It can be determined by means of ultracentrifuge measurements (W. Scholtan, H. Lange, Kolloid, Z. and Z. Polymere 250 (1972), 782-796).

Further preferred graft polymers B are, for example, also graft polymers of (a) from 20 to 90 wt. %, based on B, of acrylate rubber as graft base and
(b) from 10 to 80 wt. %, based on B, of at least one polymerisable, ethylenically unsaturated monomer, the homo- or co-polymers of which, formed in the absence of a), would have a glass transition temperature above 25° C., as graft monomers.

The graft base of acrylate rubber preferably has a glass transition temperature of less than −20° C., preferably less than −30° C.

The acrylate rubbers (a) of the polymers B are preferably polymers of acrylic acid alkyl esters, optionally with up to 40 wt. %, based on (a), of other polymerisable, ethylenically unsaturated monomers. The preferred polymerisable acrylic acid esters include $C_1$-$C_8$-alkyl esters, for example methyl, ethyl, n-butyl, n-octyl and 2-ethylhexyl ester, and mixtures of these monomers.

For crosslinking, monomers with more than one polymerisable double bond can be copolymerised. Preferred examples of crosslinking monomers are esters of unsaturated monocarboxylic acids having from 3 to 8 carbon atoms and unsaturated monohydric alcohols having from 3 to 12 carbon atoms, or saturated polyols having from 2 to 4 OH groups and from 2 to 20 carbon atoms, such as, for example, ethylene glycol dimethacrylate, allyl methacrylate; polyunsaturated heterocyclic compounds, such as, for example, trivinyl and triallyl cyanurate; polyfunctional vinyl compounds, such as di- and tri-vinylbenzenes; but also triallyl phosphate and diallyl phthalate.

Preferred crosslinking monomers are allyl methacrylate, ethylene glycol dimethacrylate, diallyl phthalate and heterocyclic compounds which contain at least 3 ethylenically unsaturated groups.

Particularly preferred crosslinking monomers are the cyclic monomers triallyl cyanurate, triallyl isocyanurate, trivinyl cyanurate, triacryloylhexahydro-s-triazine, triallylbenzenes.

The amount of crosslinking monomers is preferably from 0.02 to 5 wt. %, in particular from 0.05 to 2 wt. %, based on graft base (a).

In the case of cyclic crosslinking monomers having at least 3 ethylenically unsaturated groups, it is advantageous to limit the amount to less than 1 wt. % of the graft base (a).

Preferred "other" polymerisable, ethylenically unsaturated monomers which can optionally be used in addition to the acrylic acid esters for preparing the graft base (a) are, for example, acrylonitrile, styrene, α-methylstyrene, acrylamides, vinyl $C_1$-$C_6$-alkyl ethers, methyl methacrylate, butadiene. Preferred acrylate rubbers as the graft base (a) are emulsion polymers which have a gel content of at least 60 wt. %.

Further suitable graft bases are silicone rubbers having graft-active sites and a gel content of at least 40% (measured in dimethylformamide), as are described in Offenlegungsschriften DE 37 04 657, DE 37 04 655, DE 36 31 540 and DE 36 31 539, as well as silicone-acrylate composite rubbers.

Component C

Phosphazenes according to component C which are used according to the present invention are cyclic phosphazenes according to formula (X)

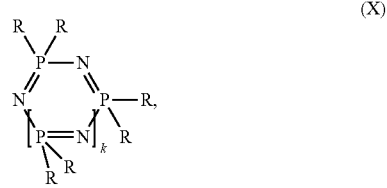

wherein

R is in each case identical or different and represents
an amine radical,
$C_1$- to $C_8$-alkyl, preferably methyl, ethyl, propyl or butyl, each optionally halogenated, preferably halogenated with fluorine, more preferably monohalogenated,
$C_1$- to $C_8$-alkoxy, preferably methoxy, ethoxy, propoxy or butoxy,
$C_5$- to $C_6$-cycloalkyl each optionally substituted by alkyl, preferably $C_1$-$C_4$-alkyl, and/or by halogen, preferably chlorine and/or bromine,
$C_6$- to $C_{20}$-aryloxy, preferably phenoxy, naphthyloxy, each optionally substituted by alkyl, preferably $C_1$-$C_4$-alkyl, and/or by halogen, preferably chlorine, bromine, and/or by hydroxy,
$C_7$- to $C_{12}$-aralkyl, preferably phenyl-$C_1$-$C_4$-alkyl, each optionally substituted by alkyl, preferably $C_1$-$C_4$-alkyl, and/or by halogen, preferably chlorine and/or bromine, or
a halogen radical, preferably chlorine or fluorine, or
an OH radical,
k has the meaning mentioned above.

Preference is given to:

propoxyphosphazene, phenoxyphosphazene, methylphenoxyphosphazene, aminophosphazene and fluoroalkylphosphazenes, as well as phosphazenes having the following structures:

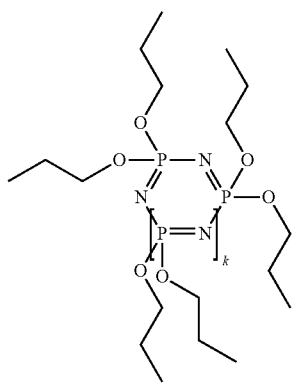

-continued

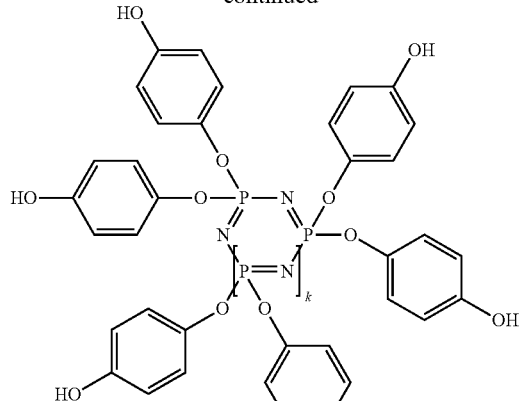

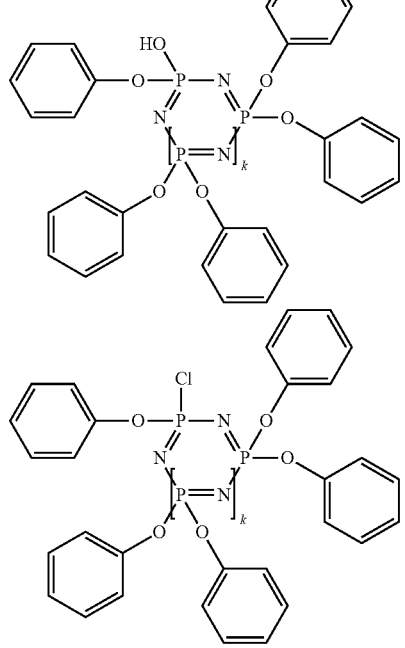

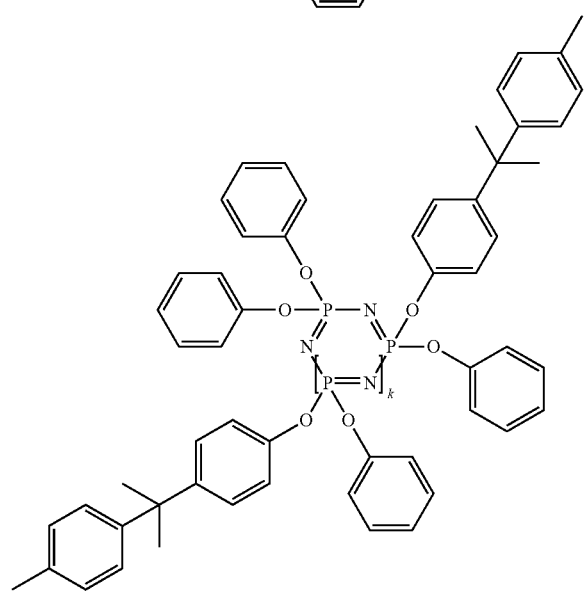

-continued

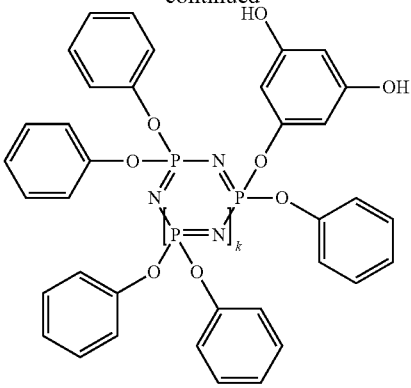

In the compounds shown above, k=1, 2 or 3.

Preference is given to phenoxyphosphazene (all R=phenoxy) having a content of oligomers with k=1 (C1) of from 60 to 98 mol %.

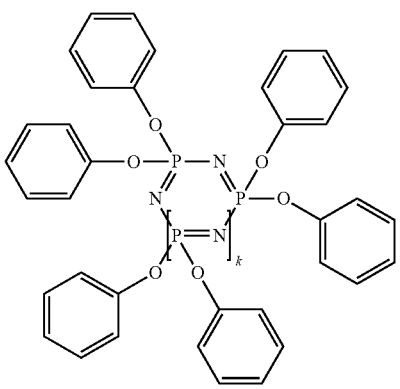

(XI)

In the case where the phosphazene according to formula (X) is halo-substituted on the phosphorus, for example from incompletely reacted starting material, the content of this phosphazene halo-substituted on the phosphorus is preferably less than 1000 ppm, more preferably less than 500 ppm.

The phosphazenes can be used on their own or in the form of a mixture, that is to say the radical R can be identical or two or more radicals in formula (X) can be different. The radicals R of a phosphazene are preferably identical.

In a further preferred embodiment, only phosphazenes with identical R are used.

In a preferred embodiment, the content of tetramers (k=2) (C2) is from 2 to 50 mol %, based on component C, more preferably from 5 to 40 mol %, yet more preferably from 10 to 30 mol %, particularly preferably from 10 to 20 mol %.

In a preferred embodiment, the content of higher oligomeric phosphazenes (k=3, 4, 5, 6 and 7) (C3) is from 0 to 30 mol %, based on component C, more preferably from 2.5 to 25 mol %, yet more preferably from 5 to 20 mol % and particularly preferably from 6 to 15 mol %.

In a preferred embodiment, the content of oligomers with k>=8 (C4) is from 0 to 2.0 mol %, based on component C, and preferably from 0.10 to 1.00 mol %.

In a further preferred embodiment, the phosphazenes of component C fulfil all three conditions mentioned above as regards the contents (C2-C4).

Component C is preferably a phenoxyphosphazene with a trimer content (k=1) of from 65 to 85 mol %, a tetramer content (k=2) of from 10 to 20 mol %, a content of higher oligomeric phosphazenes (k=3, 4, 5, 6 and 7) of from 5 to 20 mol % and of phosphazene oligomers with k>=8 of from 0 to 2 mol %, based on component C.

Component C is particularly preferably a phenoxyphosphazene with a trimer content (k=1) of from 70 to 85 mol %, a tetramer content (k=2) of from 10 to 20 mol %, a content of higher oligomeric phosphazenes (k=3, 4, 5, 6 and 7) of from 6 to 15 mol % and of phosphazene oligomers with k>=8 of from 0.1 to 1 mol %, based on component C.

In a further particularly preferred embodiment, component C is a phenoxyphosphazene with a trimer content (k=1) of from 65 to 85 mol %, a tetramer content (k=2) of from 10 to 20 mol %, a content of higher oligomeric phosphazenes (k=3, 4, 5, 6 and 7) of from 5 to 15 mol % and of phosphazene oligomers with k>=8 of from 0 to 1 mol %, based on component C.

n defines the weighted arithmetic mean of k according to the following formula:

$$n = \frac{\sum_{i=1}^{max} ki \cdot xi}{\sum_{i=1}^{max} xi}$$

where $x_i$ is the content of the oligomer $k_i$, and the sum of all $x_i$ is accordingly 1.

In an alternative embodiment, n is in the range from 1.10 to 1.75, preferably from 1.15 to 1.50, more preferably from 1.20 to 1.45, and particularly preferably from 1.20 to 1.40 (including the limits of the ranges).

The phosphazenes and their preparation are described, for example, in EP-A 728 811, DE-A 1 961668 and WO 97/40092.

The oligomer compositions of the phosphazenes in the blend samples can also be detected and quantified, after compounding, by means of $^{31}$P NMR (chemical shift; δ trimer: 6.5 to 10.0 ppm; δ tetramer: −10 to −13.5 ppm; δ higher oligomers: −16.5 to −25.0 ppm).

Component D

Component D comprises one or more thermoplastic vinyl (co)polymers or polyalkylene terephthalates.

Suitable as vinyl (co)polymers D are polymers of at least one monomer from the group of the vinyl aromatic compounds, vinyl cyanides (unsaturated nitriles), (meth)acrylic acid ($C_1$-$C_8$)-alkyl esters, unsaturated carboxylic acids and derivatives (such as anhydrides and imides) of unsaturated carboxylic acids. Particularly suitable are (co)polymers of
D.1 from 50 to 99 parts by weight, preferably from 60 to 80 parts by weight, of vinyl aromatic compounds and/or vinyl aromatic compounds substituted on the ring (such as styrene, α-methylstyrene, p-methylstyrene, p-chlorostyrene) and/or (meth)acrylic acid ($C_1$-$C_8$)-alkyl esters (such as methyl methacrylate, ethyl methacrylate), and
D.2 from 1 to 50 parts by weight, preferably from 20 to 40 parts by weight, of vinyl cyanides (unsaturated nitriles), such as acrylonitrile and methacrylonitrile, and/or (meth)acrylic acid ($C_1$-$C_8$)-alkyl esters, such as methyl methacrylate, n-butyl acrylate, tert-butyl acrylate, and/or unsaturated carboxylic acids, such as maleic acid, and/or derivatives, such as anhydrides and imides, of unsaturated carboxylic acids (for example maleic anhydride and N-phenylmaleimide).

The vinyl (co)polymers D are resin-like, thermoplastic and rubber-free. Particular preference is given to the copolymer of D.1 styrene and D.2 acrylonitrile.

The (co)polymers according to D are known and can be prepared by radical polymerisation, in particular by emulsion, suspension, solution or mass polymerisation. The (co)polymers preferably have mean molecular weights Mw (weight-average, determined by light scattering or sedimentation) of from 15,000 to 200,000 g/mol, particularly preferably from 100,000 to 150,000 g/mol.

In a particularly preferred embodiment, D is a copolymer of 77 wt. % styrene and 23 wt. % acrylonitrile with a weight-average molecular weight $M_w$ of 130,000 g/mol.

Suitable as component D the compositions comprise according to the invention one or a mixture of two or more different polyalkylene terephthalates.

Polyalkylene terephthalates within the scope of the invention are polyalkylene terephthalates which are derived from terephthalic acid (or reactive derivatives, e.g. dimethyl esters or anhydrides, thereof) and alkanediols, cycloaliphatic or aralphatic diols and mixtures thereof, for example based on propylene glycol, butanediol, pentanediol, hexanediol, 1,2-cyclohexanediol, 1,4-cyclohexanediol, 1,3-cyclohexanediol and cyclohexyldimethanol, wherein the diol component according to the invention contains more than 2 carbon atoms. Accordingly, there are used as component D preferably polybutylene terephthalate and/or polytrimethylene terephthalate, most preferably polybutylene terephthalate.

The polyalkylene terephthalates according to the invention can comprise as the monomer of the diacid also up to 5 wt. % isophthalic acid.

Preferred polyalkylene terephthalates can be prepared by known methods from terephthalic acid (or reactive derivatives thereof) and aliphatic or cycloaliphatic diols having from 3 to 21 carbon atoms (Kunststoff-Handbuch, Vol. VIII, p. 695 ff, Karl-Hanser-Verlag, Munich 1973).

Preferred polyalkylene terephthalates comprise at least 80 mol %, preferably at least 90 mol %, based on the diol component, 1,3-propanediol and/or 1,4-butanediol radicals.

As well as comprising terephthalic acid radicals, the preferred polyalkylene terephthalates can comprise up to 20 mol % of radicals of other aromatic dicarboxylic acids having from 8 to 14 carbon atoms or of aliphatic dicarboxylic acids having from 4 to 12 carbon atoms, such as radicals of phthalic acid, isophthalic acid, naphthalene-2,6-dicarboxylic acid, 4,4'-diphenyldicarboxylic acid, succinic acid, adipic acid, sebacic acid, azelaic acid, cyclohexanediacetic acid, cyclohexanedicarboxylic acid.

As well as comprising 1,3-propanediol or 1,4-butanediol radicals, the preferred polyalkylene terephthalates can comprise up to 20 mol % of other aliphatic diols having from 3 to 12 carbon atoms or cycloaliphatic diols having from 6 to 21 carbon atoms, for example radicals of 1,3-propanediol, 2-ethyl-1,3-propanediol, neopentyl glycol, 1,5-pentanediol, 1,6-hexanediol, cyclohexane-1,4-dimethanol, 3-methyl-2,4-pentanediol, 2-methyl-2,4-pentanediol, 2,2,4-trimethyl-1,3-pentanediol and 2-ethyl-1,6-hexanediol, 2,2-diethyl-1,3-propanediol, 2,5-hexanediol, 1,4-di-β-hydroxyethoxy)-benzene, 2,2-bis-(4-hydroxycyclohexyl)-propane, 2,4-dihydroxy-1,1,3,3-tetra-methyl-cyclobutane, 2,2-bis-(3-β-hydroxyethoxyphenyl)-propane and 2,2-bis-(4-hydroxypropoxy-phenyl)-propane (DE-A 24 07 674, 24 07 776, 27 15 932).

The polyalkylene terephthalates can be branched by incorporation of relatively small amounts of tri- or tetrahydric alcohols or tri- or tetra-basic carboxylic acids, as are described, for example, in DE-A 19 00 270 and U.S. Pat. No. 3,692,744. Examples of preferred branching agents are trimesic acid, trimellitic acid, trimethylol-ethane and -propane and pentaerythritol.

It is advisable to use not more than 1 mol % of the branching agent, based on the acid component.

Particular preference is given to polyalkylene terephthalates that have been prepared solely from terephthalic acid or reactive derivatives thereof (e.g. dialkyl esters thereof, such as dimethyl terephthalate) and 1,3-propanediol and/or 1,4-butanediol (polypropylene and polybutylene terephthalate) and mixtures of such polyalkylene terephthalates.

Preferred polyalkylene terephthalates are also copolyesters prepared from at least two of the above-mentioned acid components and/or from at least two of the above-mentioned alcohol components, particularly preferred copolyesters are poly-(1,3-propylene glycol/1,4-butanediol) terephthalates.

The polyalkylene terephthalates generally have an intrinsic viscosity of approximately from 0.4 to 1.5 dl/g, preferably from 0.5 to 1.3 dl/g, in each case measured in phenol/o-dichlorobenzene (1:1 parts by weight) at 25° C.

In an alternative embodiment, the polyesters prepared according to the invention can also be used in admixture with other polyesters and/or further polymers, preference being given here to the use of mixtures of polyalkylene terephthalates with other polyesters.

Further Additives E

The composition can comprise further conventional polymer additives, such as flame-retardant synergists other than antidripping agents, lubricants and demoulding agents (for example pentaerythritol tetrastearate), nucleating agents, stabilisers (for example UV/light stabilisers, heat stabilisers, antioxidants, transesterification inhibitors, hydrolytic stabilisers), antistatics (for example conductive blacks, carbon fibres, carbon nanotubes as well as organic antistatics such as polyalkylene ethers, alkyl sulfonates or polyamide-containing polymers) as well as colourants, pigments, fillers and reinforcing materials, in particular glass fibres, mineral reinforcing materials and carbon fibres.

There are preferably used as stabilisers sterically hindered phenols and phosphites or mixtures thereof, such as, for example, Irganox® B900 (Ciba Speciality Chemicals). Pentaerythritol tetrastearate is preferably used as the demoulding agent. Carbon black is further preferably used as a black pigment (e.g. Blackpearls).

As well as comprising optional further additives, particularly preferred moulding compositions comprise as component E a demoulding agent, particularly preferably pentaerythritol tetrastearate, in an amount of from 0.1 to 1.5 parts by weight, preferably from 0.2 to 1.0 part by weight, particularly preferably from 0.3 to 0.8 part by weight.

As well as comprising optional further additives, particularly preferred moulding compositions comprise as component E at least one stabiliser, for example selected from the group of the sterically hindered phenols, phosphites and mixtures thereof and particularly preferably Irganox® B900, in an amount of from 0.01 to 0.5 part by weight, preferably from 0.03 to 0.4 part by weight, particularly preferably from 0.06 to 0.3 part by weight.

Component F

As well as comprising optional further additives, particularly preferred flame-retardant compositions comprise as component F a fluorinated polyolefin in an amount of from 0.05 to 1.0 part by weight, preferably from 0.1 to 0.8 part by weight, particularly preferably from 0.2 to 0.6 part by weight.

The combination of PTFE (component F), pentaerythritol tetrastearate and Irganox B900 with a phosphorus-based flame retardant as component C) is also particularly preferred.

There are used as antidripping agents in particular polytetrafluoroethylene (PTFE) or PTFE-containing compositions such as, for example, masterbatches of PTFE with styrene- or methyl-methacrylate-containing polymers or copolymers, in the form of powders or in the form of a coagulated mixture, for example with component B.

The fluorinated polyolefins used as antidripping agents have a high molecular weight and have glass transition temperatures of over −30° C., generally over 100° C., fluorine contents of preferably from 65 to 76 wt. %, in particular from 70 to 76 wt. %, mean particle diameters $d_{50}$ of from 0.05 to 1000 μm, preferably from 0.08 to 20 μm. In general, the fluorinated polyolefins have a density of from 1.2 to 2.3 g/cm$^3$. Preferred fluorinated polyolefins are polytetrafluoroethylene, polyvinylidene fluoride, tetrafluoroethylene/hexafluoropropylene and ethylene/tetrafluoroethylene copolymers. The fluorinated polyolefins are known (see "Vinyl and Related Polymers" by Schildknecht, John Wiley & Sons, Inc., New York, 1962, pages 484-494; "Fluorpolymers" by Wall, Wiley-Interscience, John Wiley & Sons, Inc., New York, Volume 13, 1970, pages 623-654; "Modern Plastics Encyclopedia", 1970-1971, Volume 47, No. 10 A, October 1970, McGraw-Hill, Inc., New York, pages 134 and 774; "Modern Plastics Encyclopedia", 1975-1976, October 1975, Volume 52, No. 10 A, McGraw-Hill, Inc., New York, pages 27, 28 and 472 and U.S. Pat. Nos. 3,671,487, 3,723, 373 and 3,838,092).

They can be prepared by known processes, for example by polymerisation of tetrafluoroethylene in an aqueous medium with a free-radical-forming catalyst, for example sodium, potassium or ammonium peroxodisulfate, at pressures of from 7 to 71 kg/cm$^2$ and at temperatures of from 0 to 200° C., preferably at temperatures of from 20 to 100° C. (For further details see e.g. U.S. Pat. No. 2,393,967.) Depending on the form in which they are used, the density of these materials can be from 1.2 to 2.3 g/cm$^3$, and the mean particle size can be from 0.05 to 1000 μm.

The fluorinated polyolefins that are preferred according to the invention have mean particle diameters of from 0.05 to 20 μm, preferably from 0.08 to 10 μm, and density of from 1.2 to 1.9 g/cm$^3$.

Suitable fluorinated polyolefins F which can be used in powder form are tetrafluoroethylene polymers having mean particle diameters of from 100 to 1000 μm and densities of from 2.0 g/cm$^3$ to 2.3 g/cm$^3$. Suitable tetrafluoroethylene polymer powders are commercial products and are supplied, for example, by DuPont under the trade name Teflon®.

The examples which follow serve to explain the invention further.

Component A

Linear polycarbonate based on bisphenol A with a weight-average molecular weight Mw of 27,500 g/mol (determined by GPC in dichloromethane with polycarbonate as standard).

Component B

ABS graft polymer prepared by emulsion polymerisation of 43 wt. %, based on the ABS polymer, of a mixture of 27 wt. % acrylonitrile and 73 wt. % styrene in the presence of 57 wt. %, based on the ABS polymer, of a particulate crosslinked polybutadiene rubber (mean particle diameter $d_{50}$=0.35 μm).

Component C

Phenoxyphosphazene of formula (XI) having a content of oligomers with k=1 of 70 mol %, a content of oligomers with k=2 of 18 mol % and a content of oligomers with k≥3 of 12 mol %.

(XI)

[Chemical structure of phenoxyphosphazene]

Component D

Copolymer of 77 wt. % styrene and 23 wt. % acrylonitrile with a weight-average molecular weight Mw of 130 kg/mol (determined by GPC), prepared by the mass process.

Component E1

Pentaerythritol tetrastearate as lubricant/demoulding agent.

Component E2

Heat stabiliser, Irganox® B900 (mixture of 80% Irgafos® 168 and 20% Irganox® 1076; BASF AG; Ludwigshafen/ Irgafos® 168 (tris(2,4-di-tert-butyl-phenyl) phosphite)/Irganox® 1076 (2,6-di-tert-butyl-4-(octadecanoxycarbonylethyl)phenol).

Component F

Polytetrafluoroethylene powder, CFP 6000 N, Du Pont

Preparation and Testing of the Moulding Compositions

The substances listed in Table 1 are compounded at a speed of 225 rpm and with a throughput of 20 kg/h, at a machine temperature of 260° C., on a twin-screw extruder (ZSK-25) (Werner and Pfleiderer) and granulated.

The finished granules are processed on an injection-moulding machine to the corresponding test specimens (melt temperature 260° C., tool temperature 80° C., flow front speed 240 mm/s).

In order to characterise the properties of the materials, the following methods were used:

The IZOD notched impact strength was measured in accordance with ISO 180/1A on test bars of dimensions 80 mm×10 mm×4 mm overmoulded on one side.

The joint line strength anF was measured in accordance with ISO 179/1eU on a test bar measuring 80×10×4 mm overmoulded on both sides.

The behaviour in fire is measured in accordance with UL 94V on bars measuring 127×12.7×1.5 mm or 127×12.7×1.5 mm.

The tensile modulus of elasticity and the elongation at tear were determined in accordance with ISO 527 on shouldered test bars measuring 170 mm×10 mm×4 mm.

The heat distortion resistance was measured in accordance with ISO 306 (Vicat softening temperature, method B with 50 N load and a heating rate of 120 K/h) on test bars of dimensions 80 mm×10 mm×4 mm overmoulded on one side.

The melt flowability was evaluated on the basis of the melt volume-flow rate (MVR) measured in accordance with ISO 1133 at a temperature of 260° C. and with a die load of 5 kg.

As a measure of the hydrolytic stability of the prepared compositions there was used the change in the MVR measured in accordance with ISO 1133 at 260° C. with a die load of 5 kg on storage of the granules for 7 days at 95° C. and 100% relative humidity ("FWL storage"). The increase in the MVR value compared with the MVR value prior to corresponding storage was calculated as ΔMVR(hydr.), which is defined by the following formula:

$$\Delta MVR(\text{hydr.}) = \frac{MVR(\text{after } FWL \text{ storage}) - MVR(\text{prior to storage})}{MVR(\text{prior to storage})} \cdot 100\%$$

It is clear from Table 2 that only the compositions of Examples 2 to 7 with a phosphazene content of from 1.0 to 5.0 wt. % achieve the object according to the invention, that is to say a combination of high heat distortion resistance, good mechanical properties (high notched impact strength, high elongation at tear), excellent flame resistance in particular at thin wall thicknesses of 1.0 mm and good hydrolytic stability (≤20% deviation from the starting value of the MVR 260° C./5 kg after storage for 7 d/95° C./100% rel. humidity).

If the content of component C is below 1 wt. %, the flame retardancy of the moulding composition is no longer achieved; if the content is greater than 5 wt. %, the heat distortion resistance and mechanical properties diminish considerably.

TABLE 2

Composition and properties of the moulding compositions

| | Ex. 1 (comp.) | Ex. 2 | Ex. 3 | Ex. 4 | Ex. 5 | Ex. 6 | Ex. 7 | Ex. 8 | Ex. 9 (comp.) | Ex. 10 (comp.) |
|---|---|---|---|---|---|---|---|---|---|---|
| Components (parts by weight) | | | | | | | | | | |
| A | 95.6 | 95.1 | 94.6 | 94.1 | 93.6 | 93.1 | 91.6 | 91.1 | 90.1 | 91.1 |
| B | 3.0 | 3.0 | 3.0 | 3.0 | 3.0 | 3.0 | 3.0 | 3.0 | 3.0 | 3.0 |
| C | 0.5 | 1.0 | 1.5 | 2.0 | 2.5 | 3.0 | 4.5 | 5.0 | 6.0 | 7.0 |
| D | | | | | | | | | | |
| F | 0.4 | 0.4 | 0.4 | 0.4 | 0.4 | 0.4 | 0.4 | 0.4 | 0.4 | 0.4 |
| E1 | 0.4 | 0.4 | 0.4 | 0.4 | 0.4 | 0.4 | 0.4 | 0.4 | 0.4 | 0.4 |
| E2 | 0.1 | 0.1 | 0.1 | 0.1 | 0.1 | 0.1 | 0.1 | 0.1 | 0.1 | 0.1 |

TABLE 2-continued

Composition and properties of the moulding compositions

| | Ex. 1 (comp.) | Ex. 2 | Ex. 3 | Ex. 4 | Ex. 5 | Ex. 6 | Ex. 7 | Ex. 8 | Ex. 9 (comp.) | Ex. 10 (comp.) |
|---|---|---|---|---|---|---|---|---|---|---|
| Properties | | | | | | | | | | |
| Vicat B 120 | 140 | 139 | 137 | 136 | 135 | 135 | 134 | 133 | 131 | 128 |
| UL 94 V at 1.5 mm (7 d/70° C.) thickness/total afterburning time | V-1/54 s | V-0/14 s | V-0/12 s | V-0/11 s | V-0/11 s | V-0/10 s | V-0/10 s | V-0/10 s | V-0/8 s | V-0/6 s |
| UL 94 V at 1.0 mm (7 d/70° C.) thickness/total afterburning time | n.d./149 s | V-0/36 s | V-0/26 s | V-0/24 s | V-0/14 s | V-0/12 s | V-0/12 s | V-0/10 s | V-0/8 s | V-0/5 s |
| MVR 260° C./5 kg [ccm/10 min] | 11.5 | 12.4 | 12.5 | 12.7 | 12.9 | 13.0 | 13.2 | 13.3 | 16.8 | 18.1 |
| MVR 260° C./5 kg after hydrolysis (7 d/95° C./99% RH) [ccm/10 min] | 13.2 | 14.8 | | | | 15.3 | | 15.6 | | |
| delta MVR after hydrolysis [%] | 14.8 | 19.3 | | | | 17.7 | | 17.3 | | |
| Modulus of elasticity [N/mm$^2$] | 2315 | 2322 | 2329 | 2372 | 2374 | 2659 | 2691 | 2740 | 2770 | 2790 |
| Elongation at tear [%] | 135.0 | 132.2 | 129.3 | 116.8 | 116.6 | 110.4 | 109.2 | 108.3 | 92 | 78 |
| IZOD notched impact strength [kJ/m$^2$] | 66.2 | 64.5 | 62.3 | 62.1 | 62.7 | 62.6 | 59.3 | 17.7 | 15.9 | 13.2 |
| Joint line strength [kJ/m$^2$] | 127.1 | 123.1 | 120.3 | 118.2 | 116.9 | 116.9 | 116.6 | 111.5 | 109.1 | 97.2 |

The invention claimed is:
1. Composition comprising
  A) from 80 to 98 parts by weight of aromatic polycarbonate and/or aromatic polyester carbonate,
  B) from 0.5 to 6.0 parts by weight of rubber-modified graft polymer,
  C) from 0.8 to 5.0 parts by weight of at least one cyclic phosphazene according to formula (X)

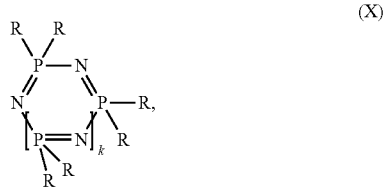

(X)

wherein
  k represents 1 or an integer from 1 to 10,
    wherein the trimer content (l=1) is from 60 to 98 mol %, wherein the content of higher oligomeric phosphazenes (k=3, 4, 5, 6 and 7) is from 5 to 20 mol %, in each case based on component C,
and wherein
  R
    is in each case identical or different and represents an amine radical; $C_1$- to $C_8$-alkyl, each optionally halogenated; $C_1$- to $C_8$-alkoxy; $C_5$- to $C_6$-cycloalkyl, each optionally substituted by alkyl and/or by halogen; $C_6$- to $C_{20}$-aryloxy each optionally substituted by alkyl, and/or by halogen, and/or by hydroxy; $C_7$- to $C_{12}$-aralkyl, each optionally substituted by alkyl, and/or by halogen; or a halogen radical; or an OH radical,
  D) from 0 to 5.0 parts by weight of rubber-free vinyl (co)polymer or polyalkylene terephthalate,
  E) from 0 to 15.0 parts by weight of one or more additives,
  F) from 0.05 to 1.00 part by weight, of one or more antidripping agents,
wherein all the parts by weight are optionally normalised that the sum of the parts by weight of all the components A+B+C+D+E+F in the composition is 100.
2. Composition according to claim 1, wherein the content of trimers (k=1) is from 65 to 95 mol %, based on component C.
3. Composition according to claim 1, wherein the amount of component C is from 1.0 to 4.5 parts by weight.
4. Composition according to claim 1, wherein component C is selected from the group consisting of propoxyphosphazenes, phenoxyphosphazenes, methylphenoxyphosphazenes, aminophosphazenes and fluoroalkylphosphazenes.
5. Composition according to claim 1, wherein R is phenoxy.
6. Composition according to claim 1, wherein the content of trimers (k=1) is from 65 to 85 mol %, based on component C.
7. Composition comprising
  A) from 80 to 98 parts by weight of aromatic polycarbonate and/or aromatic polyester carbonate,
  B) from 0.5 to 6.0 parts by weight of rubber-modified graft polymer,
  C) from 0.8 to 5.0 parts by weight of at least one cyclic phosphazene according to formula (X)

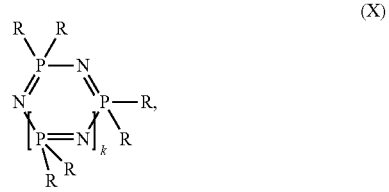

(X)

wherein
  k represents 1 or an integer from 1 to 10,
  wherein the trimer content (k=1) is from 65 to 85 mol %, the tetramer content (k=2) is from 10 to 20 mol %, the content of higher oligomeric phosphazenes (k=3, 4, 5, 6 and 7) is from 5 to 15 mol %, and the content of phosphazene oligomers with k≥8 is from 0 to 1 mol %, in each case based on component C,
and wherein
  R
    is in each case identical or different and represents an amine radical; $C_1$- to $C_8$-alkyl, each optionally halogenated; $C_1$- to $C_8$-alkoxy; $C_5$- to $C_6$-cycloalkyl, each optionally substituted by alkyl and/or by halogen; $C_6$- to $C_{20}$-aryloxy, each optionally substituted by alkyl and/or by halogen and/or by hydroxy; $C_7$- to $C_{12}$- aralkyl, each optionally substituted by alkyl and/or by halogen; or a halogen radical; or an OH radical, D) from 0 to 5.0 parts by weight of rubber-free vinyl (co)polymer or polyalkylene terephthalate, E) from 0 to 15.0 parts by weight of one or more additives, F) from 0.05 to 1.00 part by weight of one or more antidripping agents, wherein the sum of the parts by weight of all the components A+B+C+D+E+F in the composition is 100.

8. Composition according to claim 1, wherein component D) is present in an amount of from 0.5 to 4.0 parts by weight.

9. Composition according to claim 1, wherein the thermoplastic aromatic polycarbonates have a mean molecular weight (weight-average) of from 22,000 to 30,000 g/mol.

10. Composition according to claim 1, comprising as component E at least one additive selected from the group consisting of flame-retardant synergists, antidripping agents, lubricants and demoulding agents, nucleating agents, stabilisers, anti statics, colourants, pigments and fillers and reinforcing materials.

11. Composition according to claim 1, wherein the graft base of component B is selected from the group consisting of diene rubbers, EP(D)M rubbers, acrylate, polyurethane, silicone, chloroprene and ethylene/vinyl acetate rubbers.

12. A composition according to claim 1 capable of being used in production of one or more injection-moulded and/or thermoformed moulded articles.

13. Moulded article obtained from a composition according to claim 1.

14. A composition according to claim 1, wherein R is in each case identical or different and represents an amine radical; methyl, ethyl, propyl or butyl; methoxy, ethoxy, propoxy or butoxy; $C_5$- to $C_6$-cycloalkyl; phenoxy, naphthyloxy; phenyl-$C_1$-$C_4$-alkyl; or a chlorine radical; or an OH radical.

15. A composition according to claim 1, wherein R is in each case identical or different and represents an amine radical; $C_1$- to $C_8$-alkyl, each optionally halogenated with fluorine; C1- to $C_8$-alkoxy; $C_5$- to $C_6$-cycloalkyl each optionally substituted by $C_1$-$C_4$-alkyl, and/or by chlorine and/or bromine; $C_6$- to $C_{20}$-aryloxy, each optionally substituted by $C_1$-$C_4$-alkyl, and/or by chlorine and/or bromine, and/or by hydroxy; $C_7$- to $C_{12}$-aralkyl, each optionally substituted by $C_1$-$C_4$-alkyl, and/or by chlorine and/or bromine; or a halogen radical; or an OH radical.

16. A composition according to claim 1, wherein k represents 1 or an integer from 1 to 8.

17. A composition according to claim 1, wherein k represents 1 or an integer from 1 to 5.

18. Composition according to claim 1, wherein the content of trimers (k=1) is from 65 to 90 mol %, based on component C.

* * * * *